United States Patent [19]
Parks et al.

[11] 3,959,462
[45] May 25, 1976

[54] HAIR CARE PRODUCTS CONTAINING FLOUROCARBON POLYMERS FOR KEEPING HAIR CLEANER LONGER

[75] Inventors: Lawrence Roy Parks, Springfield Township, Hamilton County; Stuart Elliot Builder, Cincinnati, both of Ohio

[73] Assignee: The Procter & Gamble Company, Cincinnati, Ohio

[22] Filed: Aug. 26, 1974

[21] Appl. No.: 500,431

[52] U.S. Cl. .............................. 424/70; 252/DIG. 2; 252/DIG. 3; 252/DIG. 13; 424/DIG. 1; 424/DIG. 2; 424/71; 424/78; 424/81; 424/365
[51] Int. Cl.² ........................................... A61K 7/06
[58] Field of Search ................... 424/DIG. 4, 70, 71, 424/78, 81, DIG. 1, DIG. 2

[56] References Cited
UNITED STATES PATENTS

| | | | |
|---|---|---|---|
| 3,547,861 | 12/1970 | Anello et al. | 260/89.5 |
| 3,862,310 | 1/1975 | Quasius | 424/70 |

*Primary Examiner*—Sam Rosen
*Assistant Examiner*—Vera C. Clarke
*Attorney, Agent, or Firm*—Douglas C. Mohl; Ronald L. Hemingway; George W. Allen

[57] ABSTRACT

A process for keeping hair cleaner longer by applying to the hair a fluorine-containing polymer and products containing such polymers.

16 Claims, No Drawings

HAIR CARE PRODUCTS CONTAINING FLOUROCARBON POLYMERS FOR KEEPING HAIR CLEANER LONGER

BACKGROUND OF THE INVENTION

This invention relates to compositions containing fluorocarbon polymers which can be applied to hair to keep hair cleaner for a longer period of time.

The hair of the head has historically been associated with beauty and social distinction. This status held by hair has caused people to be concerned about its appearance and cleanliness. The scalp normally secretes more oils (sebum) than do other skin surfaces. The oil coats the hair fibers and prevents loss of moisture; it also helps to keep the hair in place and provides some luster. However, a buildup of the oil causes the hair to have a dirty feel and an unattractive appearance. This necessitates that the hair be shampooed with the subsequent result that the hair is difficult to manage.

THE PRIOR ART

A variety of approaches have been developed to alleviate the after-shampoo management problems. These range from the inclusion of hair conditioning aids in shampoos to the post shampoo application of hair conditioners, setting aids and hairsprays. These products have been designed primarily to make hair easier to manage and control by depositing a polymer film or other material onto the hair. Fluorine-containing polymers have not been used extensively in such products but have been used in some instances.

South African Pat. No. 70/7193 to Keiner discloses the application of a certain class of fluorine containing polymers to the hair either from a shampoo or from a product applied to the hair either prior to the shampooing process or after the shampooing process. The polymer is stated to reduce the time required for the hair to dry. However, Keiner does not disclose the particular fluorine-containing polymers of the present invention. Furthermore, Keiner does not teach that fluorine-containing polymers can be used for the purpose of keeping the hair cleaner for a longer period of time.

Netherlands Pat. No. 7009980-Q discloses the use of a class of fluorine containing polymers different from those of the present invention for the purpose of giving hair a permanent wave.

DESCRIPTION OF THE INVENTION

It is an object of this invention to provide hair care products and processes which will keep hair cleaner for a longer period of time than is true for current hair care products.

According to the present invention it has been found that the rate of flow of sebum along the hair shaft can be reduced by the application of a particular class of fluorinecontaining polymers to the hair. This reduction of sebum flow allows hair to remain in a cleaner state longer thereby reducing the need to shampoo as frequently.

The polymers of the present invention comprise monomeric units derived from the fluoroalcohol-containing monomers described in U.S. Pat. No. 3,547,861, issued to Gene Anello et al., Dec. 15, 1970, which patent is incorporated herein by reference. The use of emulsion polymerization products of these monomers in oral compositions is disclosed in the copending application of Lawrence R. Parks, Ser. No. 448,779, filed Mar. 6, 1974. Certain non-fluorine containing monomers, as described hereinafter, may also be used as co-monomers in preparing the polymers of the present invention.

The fluoroalcohol-containing monomers described in U.S. Pat. No. 3,547,861 have the general formula:

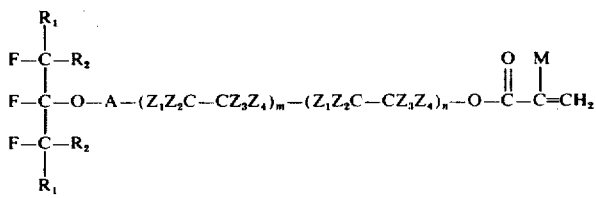

wherein a. $R_1$ and $R_2$ are each F, Cl, alkyl or haloalkyl groups, or when taken together, are alkylene or haloalkylene groups forming a cycloaliphatic structure, which $R_1$ and $R_2$ groups may each have from 1 to 9 carbon atoms and which halogen atoms, if any, have an atomic weight not exceeding about 79.91, with the proviso that no more than two of the $R_1$ and $R_2$ groups are alkyl groups and no more than three of the $R_1$ and $R_2$ groups are haloalkyl groups;

b. A is a radical of the formula $-CFR_3-CR_4R_5-$ in which $R_3$ and $R_4$ are independently selected from the group consisting of F and H, and $R_5$ is selected from the group consisting of H, F, Cl, Br and perfluoroalkyl;

c. $Z_1$, $Z_2$, $Z_3$ and $Z_4$ may each be selected from the group consisting of H, F, Cl and Br provided that $Z_1$-$Z_4$ do not include more than two chlorine atoms or one bromine atom, 1. when at least two members of the group $Z_1$, $Z_2$, $Z_3$ and $Z_4$ are H or F, the remaining two members may each be a perhalomethyl group having the formula $-C(X_a)_3$, wherein $X_a$ is a halogen atom having an atomic weight not exceeding about 79.91, 2. when $Z_1$ and $Z_3$ are each H or F, each of $Z_2$ and $Z_4$ may additionally be selected from the group consisting of $-CF_2X_b$, $-Y_1-OY_2$, $-Y_1-Y_3$ and $-O-Y_4$, wherein $X_b$ is an alkyl radical having from 1-8 carbon atoms, or a haloalkyl radical having from 1-8 carbon atoms, in which haloalkyl radical the halogen atoms have an atomic weight not exceeding about 79.91; $Y_1$ is a saturated divalent alkylene bridging group or a saturated divalent haloalkylene bridging group in which the laongen atoms have atomic weights not exceeding about 79.91; $Y_2$ is a member selected from the group consisting of H and alkyl; $Y_3$ is aryl and $Y_4$ is alkyl, 3. $Z_3$ and $Z_4$ or $Z_1$ and $Z_3$ may be joined together to form a cycloaliphatic ring system;

d. M is a member selected from the group consisting of H or $CH_3$;

e. $m$ is an integer from 1 – 75; and f. $n$ is an integer from 0 – 75.

with the proviso that the terminal carbon atom in the — $(Z_1Z_2C — CZ_3Z_4)_n$ — group which is bonded to the — O — atom is additionally bonded to two hydrogen atoms, The $Z_1$, $Z_2$, $Z_3$ and $Z_4$ substituents, as indicated above, are independently selected. This is to be interpreted as meaning that not only may the $Z_1$, $Z_2$, $Z_3$ and $Z_4$ substituents be dissimilar to one another but also that these substituents in the — $(Z_1Z_2C — CZ_3Z_4)_m$ — moiety may be dissimilar to the $Z_1$, $Z_2$, $Z_3$ and $Z_4$ substituents present in the — $(Z_1Z_2C — CZ_3Z_4)_n$ — moiety.

Specific examples of such monomers are disclosed in U.S. Pat. No. 3,547,861 at Col. 11, line 9 to Col. 14, line 27. Said examples are incorporated herein by reference.

A preferred class of monomers of the type described in the above patent have the formula:

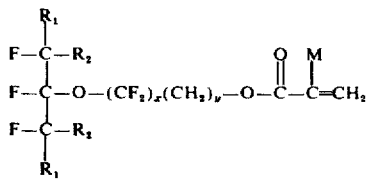

wherein $R_1$ and $R_2$ are perhaloalkyl groups having from 1-19 carbon atoms in which all the halogen atoms are selected from the group consisting of chlorine and fluorine, with the proviso that at least one fluorine is attached to each carbon atom of the $R_1$ and $R_2$ groups, M is H or $CH_3$, and $x$ and $y$ are integers from 1-20 inclusive, and may be the same or different. Examples are:

1. $(CF_3)_2CFOCF_2CF_2CH_2CH_2OCOC(CH_3) = CH_2$
2. $(CF_3)_2CFOCF_2CF_2CF_2CF_2CH_2CH_2OCOC(CH_3) = CH_2$
3. $(CF_3)_2CFOCF_2CF_2CF_2CF_2CF_2CH_2CH_2OCOC(CH_3) = CH_2$

An especially preferred monomer of this type is the one having the formula (1) above. This material is sold by Allied Chemical Corporation under the name P-4.

Optionally the polymers of the present invention may include as a co-monomer in a weight amount of 0–50%, and preferably 5–50%, of the total polymer an acrylic monomer of the following structure:

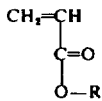

wherein R is an alkyl group, either straight or branched chain, of about 1 to 18 carbon atoms.

The acrylic monomer of the above-mentioned structur is included when it is desired to make a softer polymer than that which would be obtained from fluoro-containing monomers themselves. Examples of acceptable acrylic monomers of the above structure are butyl acrylate, 2-ethylhexylacrylate, methyl acrylate, ethyl acrylate, etc.

The polymers of the invention can be emulsion polymers which are polymerized by standard techniques for aqueous emulsion polymerization, using a cationic surface-active agent as the emulsifier. Nonionic, amphoteric or zwitterionic surface-active agents can also be used in conjunction with the cationic surface-active agent, if desired, but anionic surface-active agents should be avoided in the polymerization since these will react adversely with the cationic surface-active agent. The amount of cationic surface-active agent used in the polymerization is from about 0.01 to about 0.63 parts by weight per part by weight of monomer. Preferably, the amount of cationic surface-active agent is from about 0.1 to about 0.3 parts by weight per part by weight of monomer. (All parts and percentages herein are by weight unless specified otherwise.) If additional surface-active agents are used with the cationic surface-active agent, the amounts used should be in addition to the amount specified above for the cationic surface-active agent.

Many cationic surface-active agents are known to the art and any of these are suitable for use in the preparation of the emulsion polymers herein. By way of example, the following may be mentioned:

dodecyltrimethylammonium chloride;
nonylbenzylethyldimethylammonium nitrate;
tetradecylpyridinium bromide;
laurylpyridinium chloride;
cetylpyridinium chloride;
laurylisoquinolium bromide; and
dilauryldimethylammonium chloride.

Cationic surface-active agents which have antibacterial effectiveness, as well as surface-active properties, are especially preferred for use herein. An especially preferred cationic surface-active agent of this type is cetylpyridinium chloride.

Many additional cationic surface-active agents are described in *McCutcheon's, Detergents and Emulsifiers*, 1972 *Annual*, published by Allured Publishing Corporation, which is incorporated herein by reference.

Examples of nonionic surface-active agents which can be used in addition to the cationic surface-active agents include:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine — products which may be varied in composition depending upon the balance between the hydrophobic and hydrophilic elements which is desired. For example, compounds containing from about 40% to about 80% poloxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration, with ethylene oxide, e.g., a coconut alcohol ethylene oxide condensate having from 10 to 30 moles of ethylene oxide per mole of coconut alcohol, the coconut alcohol fraction having from 10 to 14 carbon atoms.

4. Long chain tertiary amine oxides corresponding to the following general formula:

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semi-polar bond. Examples of amine oxides suitable for use in this invention include dimethyldodecylamine oxide, oleyldi (2-hydroxyethyl)amine oxide, dimethyloctylamine oxide, dimethyldecylamine oxide, dimethyltetradecylamine oxide, 3,6,9-trioxaheptadecyldiethylamine oxide, di(2-hydroxyethyl)tetradecylamine oxide, 2-dodecoxyethyldimethylamine oxide, 3-dodexocy-2-hydroxypropyldi(3-hydroxypropyl)amine oxide, dimethylhexadecylamine oxide.

5. Long chain tertiary phosphine oxides corresponding to the following general formula:

wherein R contains an alkyl, alkenyl or monohydroxyalkyl radical ranging from 8 to 18 carbon atoms in chain length, from 0 to about 10 ethylene oxide moieties and from 0 to 1 glyceryl moiety and R' and R" are each alkyl or monohydroxyalkyl groups containing from 1 to 3 carbon atoms. The arrow in the formula is a conventional representation of a semi-polar bond. Examples of suitable phosphine oxides are:

dodecyldimethylphosphine oxide,
tetradecyldimethylphosphine oxide,
tetradecylmethylethylphosphine oxide,
3,6,9-trioxaoctadecyldimethylphosphine oxide,
cetyldimethylphosphine oxide,
3-dodecoxy-2-hydroxypropyldi(2-hydroxyethyl)-phosphine oxide,
stearyldimethylphosphine oxide,
cetylethylpropylphosphine oxide,
oleyldiethylphosphine oxide,
dodecyldiethylphosphine oxide,
tetradecyldiethylphosphine oxide,
dodecyldipropylphosphine oxide,
dodecyldi(hydroxymethyl)phosphine oxide,
dodecyldi(2-hydroxyethyl)phosphine oxide,
tetradecylmethyl-2-hydroxypropylphosphine oxide,
oleyldimethylphosphine oxide,
2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contains alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include:

octadecyl methyl sulfoxide,
2-ketotridecyl methyl sulfoxide,
3,6,9-trioxaoctadecyl 2-hydroxyethyl sulfoxide,
dodecyl methyl sulfoxide,
oleyl 3-hydroxypropyl sulfoxide,
tetradecyl methyl sulfoxide,
3-methoxytridecyl methyl sulfoxide,
3-hydroxytridecyl methyl sulfoxide,
3-hydroxy-4-dodecoxybutyl methyl sulfoxide.

Zwitterionic surface-active agents which can be used in addition to the cationic surface-active agents are those which can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

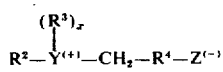

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; $x$ is 1 when Y is a sulfur atom and 2 when Y is a nitrogen or phosphorus atom; $R^4$ is an alkylene or hydroxyalkylene of from 1 to about 4 carbon atoms and Z is a radical selected from the group consisting of carboxylate, sulfonate, sulfate, phosphonate, and phosphate groups.

Examples include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate;
3-[P,P-diethyl-P-3,6,9-trioxatetradexocylphosphonio]-2-hydroxypropane-1-phosphate;
3-[N,N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl)ammonio]butane-1-carboxylate;
3-[S-ethyl-S-(3-dodecoxy-2-hydroxypropyl)sulfonio]-propane-1-phosphate;
3-(P,P-dimethyl-P-dodecylphosphonio)-propane-1-phosphonate; and
5-[N,N-di(3-hydroxypropyl)-N-hexadecylammonio]-2-hydroxypentane-1-sulfate.

The amphoteric surface-active agents which can be used in addition to the cationic surface-active agents of the invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g, carboxy, sulfonate, sulfate, phosphate, or phosphonate. Examples of compounds falling within this definition are sodium 3-dodecylaminopropionate, sodium 3-dodecylaminopropane sulfonate, N-alkyltaurines such as the one prepared by reacting dodecylamine with sodium isethionate according to the teaching of U.S. Pat. No. 2,658,072, N-higher alkyl aspartic acids such as those produced according to the teachings of U.S. Pat. No. 2,438,091, and the products sold under the trade name "Miranol" and described in U.S. Pat. No. 2,528,378.

As is conventional in the art, the aqueous emulsion polymerization is preferably carried out in a mixture wherein the amount of water is from about 1.5 to 4 times the amount of monomer, and in the presence of a catalyst or initiator which is usually an organic or inorganic free radical generator of the peroxide type. Examples of suitable catalysts are potassium or ammonium persulfate, hydrogen peroxide, sodium perborate, benzoyl peroxide, succinyl peroxide, lauryl peroxide, acetyl peroxide, cumene hydroperoxide, and the like. The catalysts are used at a level of from about 0.1% to about 1% by weight of the monomer.

The emulsion polymerization product of the invention is normally obtained from the emulsion polymerization process as a uniform, homogeneous latex of small beads having a particle size of about 0.1 micron in diameter. The solids level in the latex is from about 5% to about 40%. The molecular weight of the emulsion polymer can vary, depending on the reaction conditions, but in the present invention is of the order of about 100,000 to about 10,000,000. The particles in the latex have a coating of the cationic surface-active agent used in the polymerization. Since hair surfaces are anionic in character, the cationic coating on the polymer causes the polymer to adhere to the hair when used according to the present invention.

If desired, the polymers of the present invention may also be made using conventional solution polymerization techniques. The solution polymerization is carried out in a mixture of a halogen-containing solvent, the monomers and a catalyst which is usually an organic free radical generator of the peroxide type. Examples of suitable catalysts are benzoyl peroxide, succinyl peroxide, lauryl peroxide, acetyl peroxide, cumene hydroperoxide, 2,2'-azo-bis-2-methylpropyl nitrile, etc. Examples of suitable solvents are difluorotetrachloroethane, 1,1,2-trichloro-1,2,2-trifluoroethane, etc.

The amount of catalyst and solvent used in solution polymerization ca be adjusted by the skilled artisan so that he obtains the polymer concentration and molecular weight which he desires. In the present invention, the amount of solvent is preferably from 1.5. to 4 times the weight amount of the monomers and the catalyst is preferably used at a level of from about 0.1% to about 1% by weight of the monomers. The molecular weight of the solution polymers of the present invention can vary, depending on the reaction conditions, but generally is in the range of about 5,000 to about 300,000.

The fluorine-containing polymers of the present invention, as was discussed hereinbefore, can be used in a wide variety of hair care products. These products include, among others, such things as hair rinses, setting aids, creme rinses and shampoos. A sufficient amount of the composition is used so as to provide an effective amount (i.e., at least about 0.001 grams of the polymer to the head of human hair per usage.

A preferred mode of application of the polymers of the present invention is by means of a rinse to be used immediately after or before shampooing or at some other time between shampooings. If used after shampooing, the rinse may be left on the hair or rinsed out. The rinse comprises from about 0.01% to 7% by weight of the solid polymerization product in a liquid vehicle such as water or an organic solvent. Additionally, the rinses may contain such things as perfumes, germicides, color additives, preservatives, antioxidants, thickeners, water, ethanol, quaternary ammonium compounds, and, in the case where the polymer is solution polymerized, the rinse comprises 0.01% to 7% by weight of the polymer in halogenated hydrocarbons similar to those solvents suitable for use in the polymerization step. These include such solvents as 1,1,2-trichloro-1,2,2-trifluoroethane, difluorotetrachloroethane, etc.

The polymers of the present invention may also be applied to the hair by means of a shampoo system when they are emulsion polymerized. Solution polymers of the present invention are preferably not used in shampoos due to the necessary presence of the halogenated solvent. A major component of a shampoo system is a cleaning agent. The cleaning agents of the present invention are preferably synthetic detergents of the nonionic, zwitterionic, and amphoteric types mentioned hereinbefore. Additionally the shampoos of this invention may contain anionic detergents and soaps of fatty acids of 12–18 carbon atoms. Examples of anionic synthetic detergents include the alkylbenzene sulfonates such as sodium dodecylbenzene sulfonate, the alkyl sulfates, particularly those of the $C_{12}$–$C_{18}$ series, such as sodium lauryl sulfate and triethanolamine lauryl sulfate; the alkylbenzene polyoxyethylene sulfonates; the sulfated monoglycerides such as sodium coconut fatty acid monoglyceride sulfate; the alcohol ether sulfates; the alkyl or alkenyl sulfonates; the alkyl sulfosuccinates; alkyl sulfoacetates; alkyl taurates; alkyl sarcosinates; alkyl amide sulfonates; and alkyl isethionates.

The total level of synthetic detergents and soap may range from about 6% to about 40%. The synthetic detergents can be used singly or in combination with one another and with soap. The use of anionic synthetic detergents alone is not particularly desirable since the anionic detergent tends, in some instances, to interfere with the ability of the polymer to adhere to the hair.

The shampoos of the present invention in addition to the cleaning agets and the fluorine-containing cationic polymer may contain other conventional shampoo ingredients. These include additional water, pH adjusting agents such as citrates, phosphates, borates and carbonates as well as acids and bases such as HCl and NaOH. The pH of the shampoos of the present invention may range from about 4 to about 8 and preferably from about 6.5 to about 7.5. The shampoos contain from about 0.1% to 7% by weight of the solid polymerization product.

It is also desirable to include among other things suspending agents (e.g., montmorillonite clays), thickening agents (e.g., polyethylene glycol distearate), preservatives (e.g., benzyl alcohol), antidandruff agents (e.g., sulfur), suquestering agents (e.g., citric acid), perfumes, antibacterial agents (e.g., adipic acid), conditioning agents (e.g., quaternary ammonium compounds), and dyes.

The following examples are given to further illustrate and in no way to limit this invention. The percentages shown in the specification and the claims are by weight unless otherwise designated.

EXAMPLE I

A 2-liter reaction vessel equipped with an electrical stirrer was charged with 150 grams of Allied Chemical's P-4 monomer (3,3,4,4-tetrafluoro-4-(heptafluoroisopropoxy)butylmethacrylate), 6.615 grams of cetyl pyridinium chloride, 0.75 grams of ammonium persulfate and 660 grams of distilled water. The mixture was stired for 3 hours at 70°C. under a nitrogen atmosphere. The resulting polymerization product was a latex having a solids content of 18.7% having a molecular weight of approximately 1,000,000.

EXAMPLE II

A 2-liter reaction vessel equipped with an electrical stirrer was charged with 80 grams of distilled water, 1.25 grams of cetyl pyridinium chloride, 21.5 grams of Allied Chemical's P-4 monomer (3,3,4,4-tetrafluoro-4-(heptafluoroispropoxy)butyl methacrylate) and 3.5 grams of 2-ethyl hexyl acrylate. This mixture was stirred for approximately thirty minutes after which time 0.3 grams of ammonium persulfate and 20 additional grams of distilled water were added. The total mixture was stirred for 2 hours at 70°C. under a nitrogen atmosphere. The resulting polymerization product was a latex having a solids content of 9.2% having a molecular weight of approximately 1,000,000.

EXAMPLE III

A 2-liter reaction vessel equipped with an electrical stirrer was charged with 164.5 grams of difluorotetrachloroethane, 129 grams of Allied Chemical's P-4 monomer (3,3,4,4-tetrafluoro-4-(heptafluoroisopropoxy)butylmethacrylate, 2.1 grams of 2-ethylhexyl acrylate, and 0.25 grams of 2,2'-azo bis-2-methylpropyl nitrile. The mixture was stirred for 5 hours at 70°C. under a nitrogen atmosphere. The resulting solution polymerization product had a solids content of 12.02% and a molecular weight of approximately 200,000.

EXAMPLE IV

Four hair switches were made using approximately 100 hairs (0.3 grams weight) each. The root ends of the switches were taped with the switches then being shampooed with the same shampoo and dried at ambient conditions (~70°F.).

The solutions selected for determining their effectiveness in terms of preventing sebum flow were as follows:

| Solution | |
|---|---|
| A | 0.1% Hexafluoroisopropyl methacrylate emulsion polymer in water (a prior art polymer disclosed by Keiner, S.Af. Pat. No. 70/7193) |
| B | 0.1% The polymer of Example II |
| C | 0.1% Tame Creme Rinse (The Gillette Co., Toni Division, Chicago, Illinois 60654) |
| D | Distilled water. |

Each switch was treated with a different solution. The matchup of solutions and switches was as follows:

| Solution | Switches |
|---|---|
| A | 1 |
| B | 2 |
| C | 3 |
| D | 4 |

Each switch was placed in its appropriate solution for 15 seconds after which time the switches were rinsed with distilled water and dried for 1½ hours at ambient conditions (~70°F.). The dried switches were vertically positioned on a rod and were placed in a room at 98.6°F. so that the tips of the switches were allowed to touch an artificial sebum composition. The artificial sebum was a combination of squalane, fatty acids and other fatty materials.

The switches were allowed to remain in contact with the artificial sebum for 45 minutes and were then placed in osmium tetroxide desiccator for 60 minutes.

The rise of the sebum on each switch was measured. The rise of sebum on the switch that had been treated with distilled water was used as a standard and the other switches were compared with it. The results of the test solutions were as follows:

| Solution | % Sebum Rise Relative to Water |
|---|---|
| A | 29% |
| B | 13 |
| C | 53 |

The above test was repeated with the following results:

| Solution | % Sebum Rise Relative to Water |
|---|---|
| A | 28% |
| B | 18 |
| C | 63 |

EXAMPLE V

The following shampoo composition is prepared:

| Ingredient | % by Weight |
|---|---|
| N-(3-coconutacylamidopropyl)-N,N-dimethyl-2-aminoacetate | 4.0 |
| Sodium polyethoxylated (3) lauryl sulfosuccinate monoester | 8.2 |
| Polymer of Example II | 2.0 |
| Polyethoxylated (206 moles) polypropylene glycol, molecular weight 10,800 | 14.0 |
| Perfume | 0.5 |
| Water | balance |

EXAMPLE VI

The following hair rinse composition is prepared:

| Ingredient | % by Weight |
|---|---|
| Polymer of Example III | 2.00 |
| Perfume | 0.5 |
| Ethyl alcohol | 3.0 |
| Trichlorotrifluoro ethane | balance |

What is claimed is:

1. A method of reducing the rate of sebum flow comprising applying to hair a composition comprising from 0.01% to 7% of a polymerization product of:

A. 50% to 100% by weight of a monomer having the following structure:

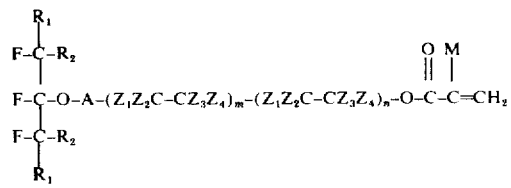

wherein
1. $R_1$ and $R_2$ are each F, Cl, alkyl or haloalkyl groups, or when taken together, are alkylene or haloalkylene groups forming a cycloaliphatic structure, which $R_1$ and $R_2$ groups may each have from 1 to 9 carbon atoms and which halogen atoms, if any, have an atomic weight not exceeding about 79.92, with the proviso that no more than two of the $R_1$ and $R_2$ groups are alkyl grops and no more than three of the $R_1$ and $R_2$ groups are haloalkyl groups;
2. A is a radical of the formula $-CFR_3-CR_4R_5-$ in which $R_3$ and $R_4$ are independently selected from the group consisting of F and H, and $R_5$ is selected from the group consisting of H, F, Cl, Br and perfluoroalkyl;
3. $Z_1, Z_2, Z_3$ and $Z_4$ may each be selected from the group consisting of H, F, Cl and Br provided that $Z_1 - Z_4$ do not include more than two chlorine atoms or one bromine atom,
   a. when at least two members of the group $Z_1, Z_2, Z_3$ and $Z_4$ are H or F, the remaining two members may each be a perhalomethyl group having the formula $-C(X_a)_3$, wherein $X_a$ is a halogen atom having an atomic weight not exceeding about 79.91,
   b. when $Z_1$ and $Z_3$ are each H or F, each of $Z_2$ and $Z_4$ may additionally be selected from the group consisting of $-CF_2X_b$, $-Y_1-OY_2$, $-Y_1-Y_3$ and $-O-Y_4$ wherein $X_b$ is an alkyl radical having from 1 to 8 carbon atoms, or a haloalkyl radical having from 1 to 8 carbon atoms in which haloalkyl radical the halogen atoms have an atomic weight not exceeding about 79.91; $Y_1$ is a saturated divalent alkylene bridging group or a saturated divalent haloakylene bridging group in which the halogen atoms have atomic weights not exceeding about 79.91; $Y_2$ is a member selected from the group consisting of H and alkyl; $Y_3$ is aryl and $Y_4$ is alkyl,
   c. $Z_3$ and $Z_4$ and $Z_1$ and $Z_3$ may be joined together to form a cycloaliphatic ring system;
4. M is a member selected from the group consisting of H or $CH_3$,
5. m is an integer from 1 to 40; and
6. n is an integer from 0 to 40, with the proviso that the terminal carbon atom in the $-(Z_1Z_2C-CZ_3Z_4)$ — group which is bonded to the $-O-$ atom is additionally bonded to two hydrogen atoms; and B. 0 to 50% by weight of a monomer of the following structure:

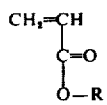

wherein R is an alkyl group either straight or branched chain, of about 4 to 18 carbon atoms, and wherein the molecular weight of the polymer is from about 100,000 to about 10,000,000 when the polymer is an emulsion polymer, and from about 5,000 to about 300,000 when the polymer is a solution polymer;

wherein said composition is applied in amounts effective to provide at least about 0.001 grams of said polymer to the head per usage.

2. The method of claim 1 wherein the polymerization product is an emulsion polymer.

3. The method of claim 2 wherein the monomer of (A) has the following structure:

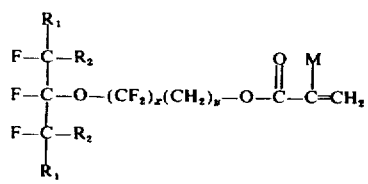

wherein $R_1$ and $R_2$ are perhaloalkyl groups having from about 1 to 19 carbon atoms in which all the halogen atoms are selected from the group consisting of chlorine and fluorine, with at least one fluorine attached to each carbon atom of the $R_1$ and $R_2$ groups, M is H or $CH_3$, and x and y are integers from about 1 to 20 inclusive and may be the same or different.

4. The method of claim 2 wherein the monomer of (A) is 3,3,4,4-tetrafluoro-4-heptafluoroisopropoxy)-butylmethacrylate.

5. The method of claim 1 wherein the polymerization product is a solution polymer.

6. The method of claim 5 wherein the monomer of (A) has the following structure:

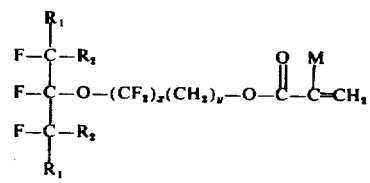

wherein $R_1$ and $R_2$ are perhaloalkyl groups having from about 1 to 19 carbon atoms in which all the halogen atoms are selected from the group consisting of chlorine and fluorine, with at least one fluorine attached to each carbon atom of the $R_1$ and $R_2$ groups, M is H or $CH_3$, and x and y are integers from about 1 to 20 inclusive and may be the same or different.

7. The method of claim 5 wherein the monomer of (A) is 3,3,4,4-tetrafluoro-4-(heptafluoroisopropoxy)-butylmethacrylate.

8. A hair care composition for use in retarding the rate of sebum flow on hair containing a liquid carrier and from 0.01% to 7% of a polymerization product of:
   A. 50% to 95% by weight of a monomer having the following structure:

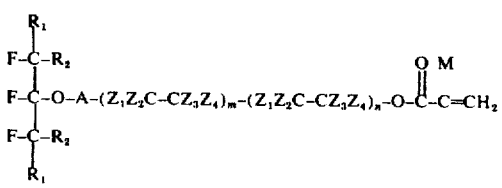

wherein
1. $R_1$ and $R_2$ are each F, Cl, alkyl or haloalkyl groups, or when taken together, are alkylene or haloalkylene groups forming a cycloaliphatic structure, which $R_1$ and $R_2$ groups may each have from 1 to 9 carbon atoms and which halogen atoms, if any, have an atomic weight not exceeding about 79.92, with the proviso that no more than two of the $R_1$ and $R_2$ groups are alkyl groups and no more than three of the $R_1$ and $R_2$ groups are haloalkyl groups;
2. A is a radical of the formula $—CFR_3—CR_4R_5—$ in which $R_3$ and $R_4$ are independently selected from the group consisting of F and H, and $R_5$ is selected from the group consisting of H, F, Cl, Br and perfluoroalkyl;
3. $Z_1$, $Z_2$, $Z_3$ and $Z_4$ may each be selected from the group consisting of H, F, Cl and Br provided that $Z_1 - Z_4$ do not include more than two chlorine atoms or one bromine atom,
   a. when at least two members of the group $Z_1$, $Z_2$, $Z_3$ and $Z_4$ are H or F, the remaining two members may each be a perhalomethyl group having the formula $—C(X_a)_3$, wherein $X_a$ is a halogen atom having an atomic weight not exceeding about 79.91,
   b. when $Z_1$ and $Z_3$ are each H or F, each of $Z_2$ and $Z_4$ may additionally be selected from the group consisting of $—CF_2X_b$, $—Y_1—OY_2$, $—Y_1—Y_3$ and $—O—Y_4$ wherein $X_b$ is an alkyl radical having from 1 to 8 carbon atoms, or a haloalkyl radical having from 1 to 8 carbon atoms in which haloalkyl radical the halogen atoms have an atomic weight not exceeding about 79.91; $Y_1$ is a saturated divalent alkylene bridging group or a saturated divalent haloalkylene bridging group in which the halogen atoms have atomic weights not exceeding about 79.91; $Y_2$ is a member selected from the group consisting of H and alkyl; $Y_3$ is aryl and $Y_4$ is alkyl,
   c. $Z_3$ and $Z_4$ and $Z_1$ and $Z_3$ may be joined together to form a cycloaliphatic ring system;
4. M is a member selected from the group consisting of H or $CH_3$,
5. m is an integer from 1 to 40; and
6. n is an integer from 0 to 40, with the proviso that the terminal carbon atom in the $—(Z_1Z_2C — CZ_3Z_4)—$ group which is bonded to the $—O—$ atom is additionally bonded to two hydrogen atoms; and B. 5% to 50% by weight of a monomer of the following structure:

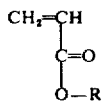

wherein R is an alkyl group either straight or branched chain, of about 4 to 18 carbon atoms, and wherein the molecular weight of the polymer if from about 100,000 to about 10,000,000 when the polymer is an emulsion polymer, and from about 5,000 to about 300,000 when the polymer is a solution polymer.

9. The hair care composition of claim 8 wherein the polymerization product is an emulsion polymer.

10. The hair care composition of claim 9 wherein the monomer of (A) has the following structure:

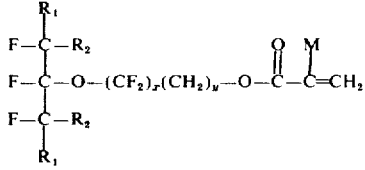

wherein $R_1$ and $R_2$ are perhaloalkyl groups having from about 1 to 19 carbon atoms in which all the halogen atoms are selected from the group consisting of chlorine and fluorine, with at least one fluorine attached to each carbon atom of the $R_1$ and $R_2$ groups, M is H or $CH_3$, and x and y are integers from about 1 to 20 inclusive and may be the same or different.

11. The hair care composition of claim 9 wherein the monomer of (A) is 3,3,4,4-tetrafluoro-(heptafluoroisopropoxy)butylmethacrylate.

12. The hair care composition of claim 8 wherein the polymerization product is a solution polymer.

13. The hair care composition of claim 12 wherein the monomer of (A) has the following structure:

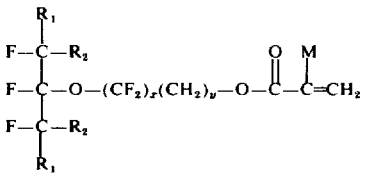

wherein $R_1$ and $R_2$ are perhaloalkyl groups having from about 1 to 19 carbon atoms in which all the halogen atoms are selected from the group consisting of chlorine and fluorine, with at least one fluorine attached to each carbon atom of the $R_1$ and $R_2$ groups, M is H or $CH_3$, and x and y are integers from about 1 to 20 inclusive and may be the same or different.

14. The hair care composition of claim 12 wherein the monomer of (A) is 3,3,4,4-tetrafluoro-4-heptafluoroisopropoxy)butylmethacrylate.

15. The hair care composition according to claim 9 which is a shampoo and which additionally contains from about 6% to about 40% of a cleaning agent.

16. The composition of claim 15 wherein the monomer of (A) is 3,3,4,4-tetrafluoro-4-(heptafluoroisopropoxy)butylmethacrylate.

* * * * *